US00PP08675P

United States Patent [19]

Yamashita et al.

[11] Patent Number: Plant 8,675

[45] Date of Patent: Apr. 5, 1994

[54] WHITE DOGWOOD TSUKUBA-NO-MINE

[76] Inventors: Nobuo Yamashita, 930-1, Fujimagari, Oyama-machi, Sunto-gun, Shizuoka; Hisao Ishikawa, 3451, Kamiyamakawa, Oaza, Yuki-shi, Ibaragi; Toshihiro Hagiwara, 334, Kaminoda, Oaza, Urawa-shi, Saitama, all of Japan

[21] Appl. No.: 919,269

[22] Filed: Jul. 27, 1992

[30] Foreign Application Priority Data

Aug. 1, 1991 [JP] Japan ..... 3-4659

[51] Int. Cl.[5] ..... A01H 5/00

[52] U.S. Cl. ..... Plt./53.2

[58] Field of Search ..... Plt. 53.2

*Primary Examiner*—James R. Feyrer

*Attorney, Agent, or Firm*—Sandler, Greenblum and Bernstein

[57] ABSTRACT

A new and distinct variety, of *Cornus kousa*, called "Tsukuba-No-Mine" of white dogwood plant substantially as herein shown and described, characterized particularly as to novelty by the unique combination of (1) upright growth habit with thin branches and high branching characteristics; (2) small leaves; (3) flowering in a period from early to late June, over approximately 20 days; (4) blossoms being yellowish white; and (5) blossoms having thin patulous of narrow substantially lanceolate-shape of approximately 0.9 to 1.2 cm in width, and small diameter of approximately 6 to 7 cm.

5 Drawing Sheets

BACKGROUND AND SUMMARY OF THE DISCLOSURE

The present disclosure is drawn to a highly unusual member of the *Cornus kousa* family. In 1978, 20 liters of seeds were harvested from dogwood trees growing in the area around Numata-shi, Gunma-ken, Japan. Such seeds were sown, en masse, the following spring and a large number of saplings resulted. The seedlings were allowed to grow, and among the population, one plant was distinctly different, having thinner branches and smaller leaves. Based on these unusual traits, the plant was selected for further observation and testing, labeled and transplanted in March, 1982.

Following transplanting, the observation of the selection, which grew to height of 2.0 m by 1984, was continued. In June of 1984, three blossoms were presented. In observing the blossoms, it was immediately noticed that the blossoms were uniquely distinct from those of normal plants of the species, and were characterized by narrower bracts, which tapered to points, blossoms of smaller diameter, and by having a differing flowering period.

The new variety "Tsukuba-No-Mine" expresses the following distinct characteristics:

(1) an upright growth habit with thin branches and high branching characteristics;
(2) small leaves;
(3) flowering in a period from early to late June, over approximately 20 days;
(4) blossoms being yellowish white, No. 2901 in the Japanese Color Code;
(5) blossoms having four thin bracts of substantially lanceolate-shape, of 0.9 to 1.2 cm in width, and having a small diameter, of approximately 6 to 7 cm;
(6) leaves being strong green, No. 4306 in the Japanese Color Code, and No. 132B in The Royal Horticultural Society Color Chart; and
(7) fruit are small, of about 1.5 cm in diameter, and yield 3 to 5 seeds. Fruit mature to a red color.

BRIEF DESCRIPTION OF THE PHOTOGRAPHS

In the accompanying photographs:

DETAILED DESCRIPTION OF THE NEW VARIETY

The following description was made of plants growing at Yuki-shi, Ibaragi-ken, Japan. Color terminology is in accordance with the ISCC-NBS method of designating colors in the United States for the literal descriptions of the colors, followed by the numerical designation for the specific color as taken from The Japan Standard Horticultural Color Chart. Selective color values are specified through reference to The Royal Horticultural Society Color Chart where appropriate for conveient comparisons.

Parentage And Growth History

Our plant originated as a seedling selected from a population attained from a seed collected from native dogwood trees growing in the area around Numata-shi, Gunmaken, Japan in October, 1978. Two liters of seeds were originally collected. In the spring of 1979, the seeds were germinated, planted en masse, and produced about 1500 seedlings. In the spring of 1982, one individual plant was discovered to differ substantially from the other seedlings by having thinner branches and smaller leaves. This unusual plant was removed from the population and transplanted into a nursery where it was individually cared for and fertilized. After a period of six years, the selection had attained a height of 2 meters, a spread of the selection in plan view of 0.8 meters, and had flowered for the first time. In subsequent seasons, the plant has been observed to be a stable and regularly flowering plant. By June, 1991, the original specimen had grown to a height of 4.5 meter, had attained a trunk diameter of 6 cm (calculated from a trunk circumference of 0.18 meter), measured at a height of about 1.2 meters, and a spread of 2.0 meters.

Growth Habit

The claimed variety "Tsukuba-No-Mine" has an upright limb growth habit, with heavily branching characteristics and thin branches.

We have asexually reproduced the claimed tree by both grafting and rooting of cuttings at our production facilities in Yuki-shi, Ibaragi-ken, Japan, and found the ramets of the tree to be identical to the individually selected specimen in all distinguishing characteristics.

Blossoms

The blossoms are highly attractive and have a yellowish white color, i.e., No. 2901 in the Japanese Color Code. The typical size of the blossoms is approximately 6 to 7 cm. The blossom has narrow lanceolate-bracts of 0.9 to 1.2 cm in width (see FIG. 2).

Trunk and Branches

The claimed variety "Tsukuba-No-Mine" has no external appearance approximately 4.5 meter in height, has attained a trunk diameter of 6 cm (at 1.2 meters) and a spread of 2.0, meter at the present. Ramets of the tree develop into small trees having a single trunk and a weakly dominant central leader. Tree form may be attained with minimal basal pruning. Specimens have strongly ascending branches which join the central leader in strong union of about 45° angles. Trees are not basally dominant, and form into densely branched and foliated specimens of narrow upright figure.

Figure 4:
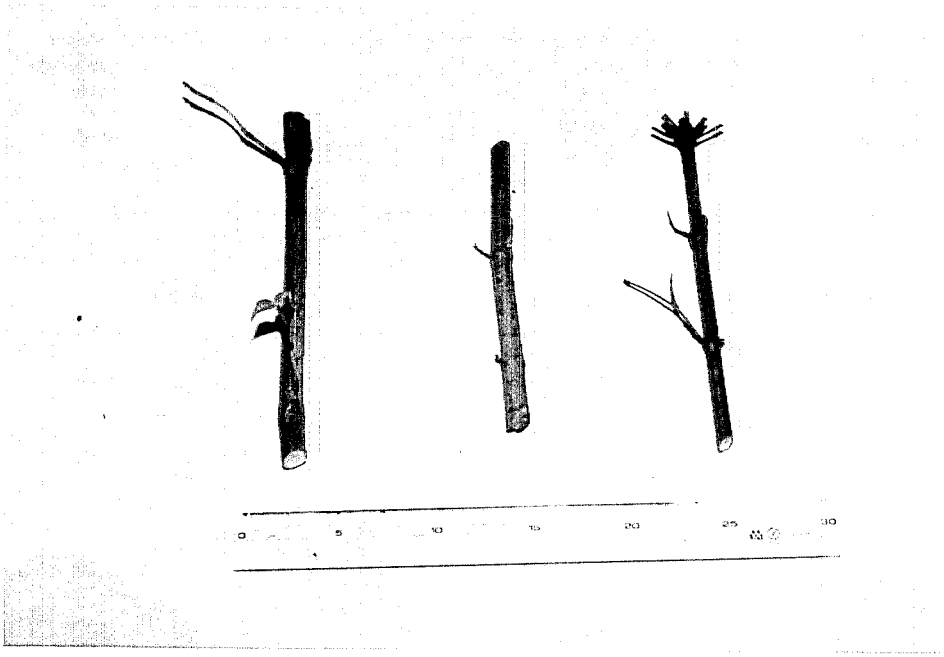
FIG. 4 shows a comparison of the bark of the claimed variety "Tsukuba-No-Mine" (right), the wild variety (center), and "Miss Satomi" (left)

The color of the bark is green in the first year, and then changes to a grayish white in the next year, getting darker and darker in the following years. The bark becomes darker than the wild *Cornus kousa* comparison variety. The texture of the bark is fine. Otherwise, the bark is not different than that of the wild *Cornus kousa* comparison variety. FIG. 4 shows the bark of "Tsukuba-No-Mine," the wild variety and "Miss Satomi", from right to left.

Foliage

Figure 2:
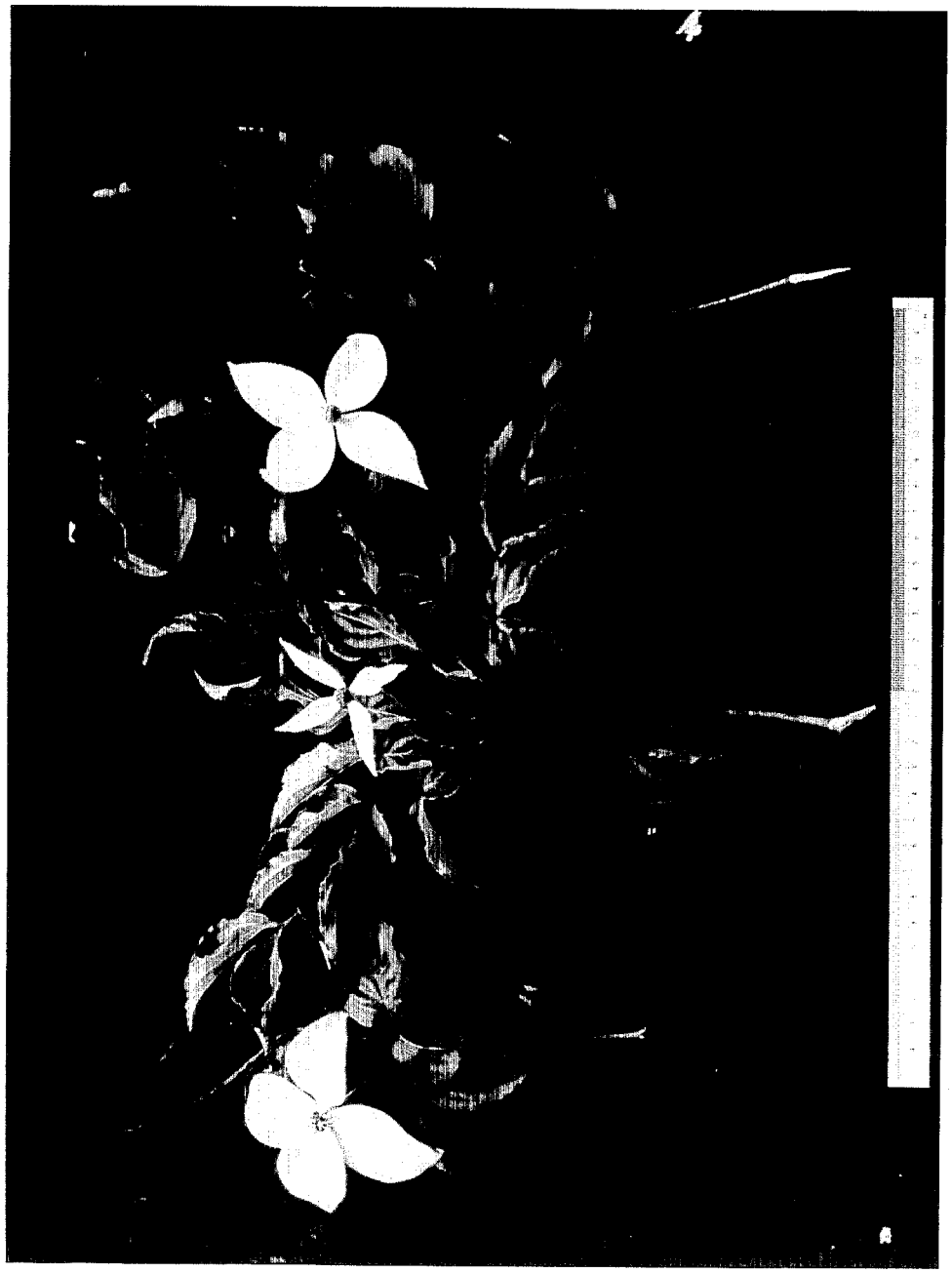
FIG. 2 shows comparison of the claimed variety "Tsukuba-No-Mine" (center) and the comparative varieties, i.e., variety known as "Miss Satomi" (left) and a wild variety (right)
Figure 3:
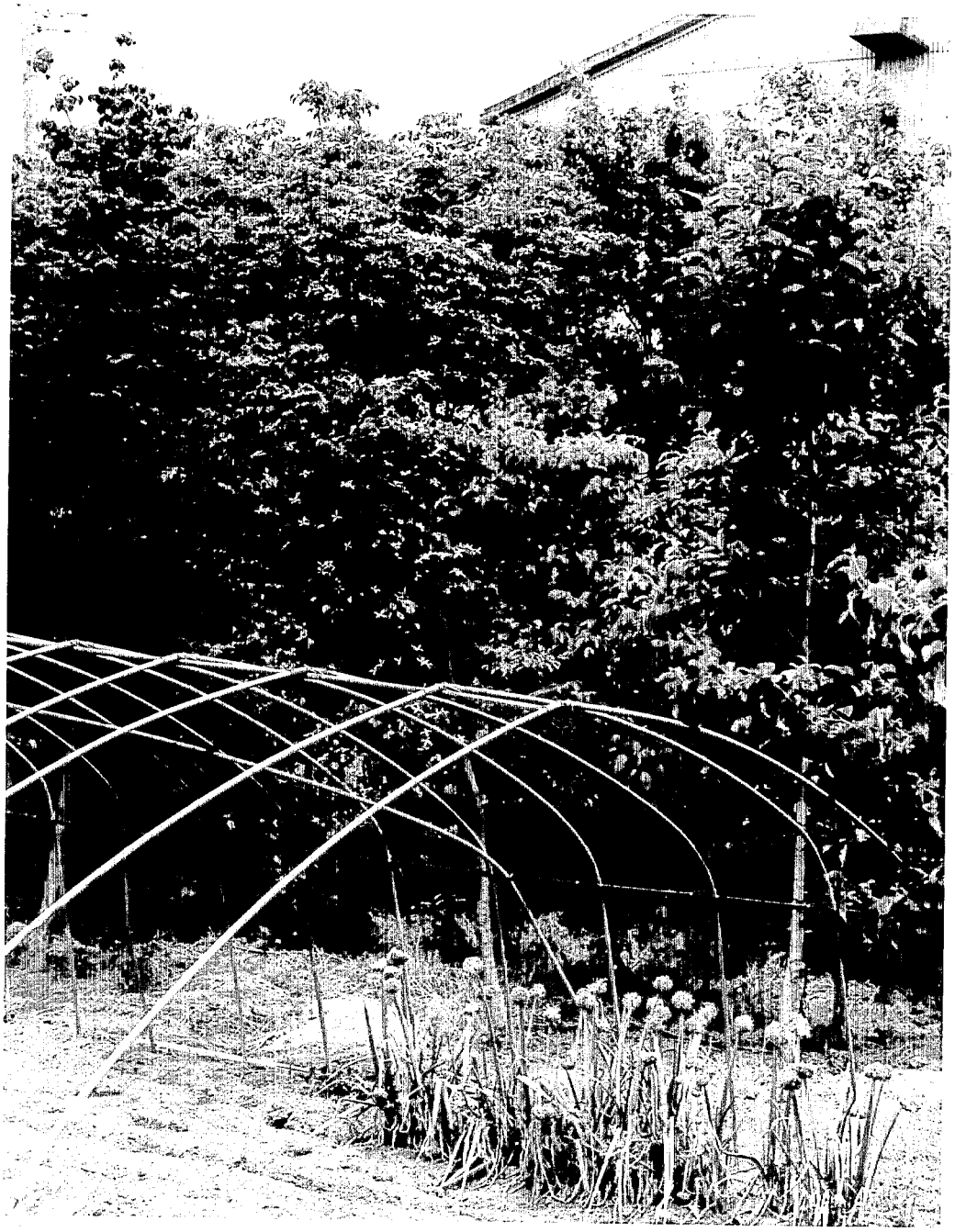
FIG. 3 shows a parent plant of the claimed variety "Tsukuba-No-Mine"

The claimed variety "Tsukuba-No-Mine" has small leaves unique among a wide variety of dogwoods as particularly seen in FIG. 2. Further details of the foliage are as follows:

Size:

"*Tsukuba-No-Mine*".—5–8 cm long, 3–4 cm wide.

*Wild Cornus kousa*.—8–11 cm long, 5–6 cm wide.

"*Miss Satomi*".—9–12 cm long, 7–9 cm wide.

Shape: Leaves of the claimed trees are more lanceolate and less oval than those of the comparison trees.

Color: The leaves of the claimed plant "Tsukuba-No-Mine" are shown to be of a lighter green color than those of either comparison plant. The fall colors of the leaves are as follows, with reference to the Japanese Color Code Nos.: No. 1305–1306 for "Tsukuba-No-Mine"; No. 0705–0706 for wild *Cornus kousa*; and No. 0705–0706 for "Miss Satomi."

The color of the leaf stems are green, and lighter than the color of the leaves. Each of "Tsukuba-No-Mine," the wild *Cornus kousa*, and Miss Satomi have a color identified by Japanese color Code No. 3511.

Characteristics of the margin: The margins of the leaves of each tree crenate and entire; but the margins of leaves of the claimed "Tsukuba-No-Mine" tree have heavy undulations when compared to the other two varieties.

Attitude and positioning: The leaves of "Tsukuba-No-Mine" reflex to a higher degree and are involute to an extent which allows for the opposite margins to nearly clasp on some leaves, while the leaves of both comparison trees are much more planer and imbricated in relative positions.

Tomentum: "Tsukuba-No-Mine," the wild *Cornus kousa*, and "Miss Satomi" have almost equal density, color, and attitude of tomenta, that exists only in a few delta areas (where venation and a midrib join) on a bottom surface of each leaf.

Glabrousness: There is no difference among the three varieties in this respect.

Figure 5:
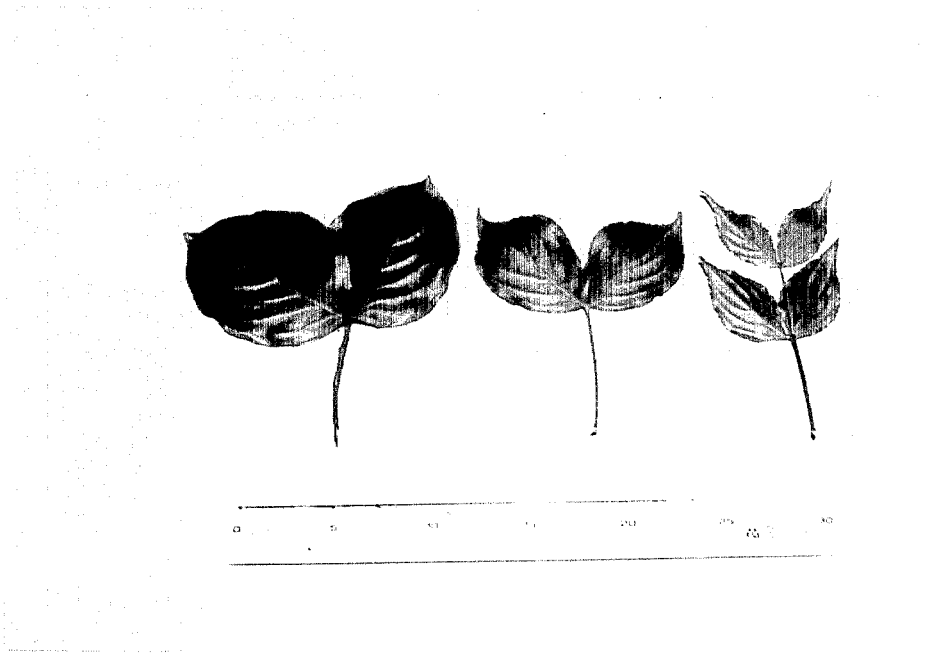
FIG. 5 shows a comparison of the bottom surface of the foliage of, from right to left, "Tsukuba-No-Mine", the wild variety and "Miss Satomi"
Figure 6:
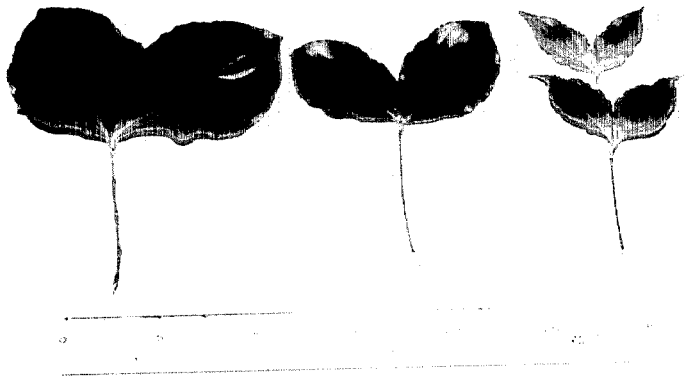
FIG. 6 shows a top surface of (from right to left) the claimed variety "Tsukuba-No-Mine," the wild variety and "Miss Satomi."

The degree of contrast between the top and bottom surfaces of the leaves is seen most clearly with reference to the photographs of FIGS. 5 and 6.

Timing of color change in the fall: The foliage turns red in the first or second ten days of November.

Fruit: Fruit appear in the summer and mature the first or second ten days of September. They are edible, taste like jelly and are sweet. Birds, also eat them. These traits are common to the *Cornus kousa* varieties.

Comparative Varieties

To demonstrate the distinctiveness of the claimed variety "Tsukuba-No-Mine," two known varieties, i.e., the variety known as "Miss Satomi" and a wild variety which was observed in Yuki-shi, Ibaragi-ken, Japan, have been compared. To enable a clear comparison, experimental cultivation was performed with the claimed variety "Tsukuba-No-Mine" and comparative varieties, i.e., the variety known as "Miss Satomi" and a wild variety of *Cornus kousa*.

Figure 1:
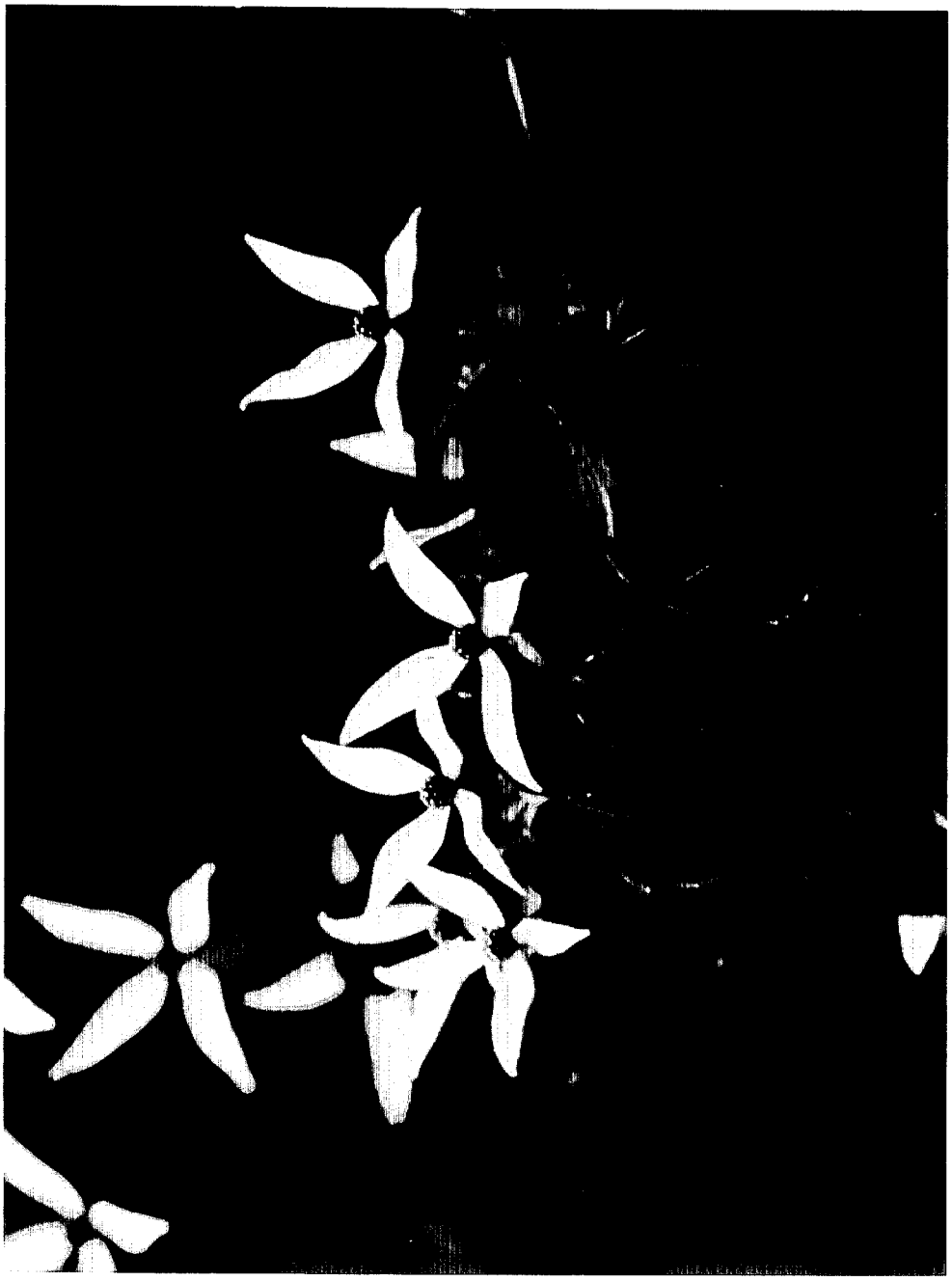
FIG. 1 shows a typical specimen of the new variety, the color of which is as nearly true as possible with color illustration of this character.

The "Tsukuba-No-Mine" was grafted in March 1989, along with the variety "Miss Satomi." Specimens of each plant were planted along with a wild specimen *Cornus kousa* on its own stock for comparison of growth characteristics at the cultural location noted above, in March of 1990. These specimens were pruned in December of 1990 by trimming the lower branches. In June of 1990 blossoms and foliage as depicted in FIG. 1 were observed on the "Tsukuba-No-Mine," but "Miss Satomi" and the wild specimen had not yet come into the flowering stage, even though each specimen had received chemical fertilizer treatments in winter and spring. Specimens had attained a height of 1.2 meter and a width of 0.6 meter for "Tsukuba-No-Mine," a height of 1.5 meter and a width of 0.6 meter for "Miss Satomi,"

and a height of 2.0 meter and a width of 0.8 meter for the wild specimen.

In further observations of the "Tsukuba-No-Mine," the following characteristics have been observed to botanically characterize the tree:

Figure: Narrow upright, cup shaped.
Size: Moderately tall.
Trunk: Thin.
Branches:
*Color.*—Gray brown.
*Branching.*—Densely ramose.
*Joint span.*—Small, joint angles are about 45°.
Foliage:
*Shape.*—Ovate-lanceolate.
*Tips.*—Acuminate.
*Bases.*—Attenuate.
*Size.*—Small.
*Color.*—RHS 132B for the top surface.
*Hair.*—Present only in delta areas where venation and mid-ribs join on the bottom surface, the hair are fine, short and dense.
*Leaf stem.*—Short, green, sunburned portions grow reddish-brown.
Blossoms:
*Pose.*—Upward.
*Character.*—Single involucre of four non-overlapped bracts.
*Size.*—Small.
*Bracts.*—Lanceolate, thin.
*Color.*—Yellowish white; Japanese Color Code No. 2901.
*Pedicel.*—3.0 to 3.5 cm.
*Fragrance.*—None.
Fruit:
*Shape.*—Round.
*Size.*—1.5 cm in diameter.
*Seeds.*—3 to 5 per fruit.
*Color.*—Moderate Red Orange; RHS 35B, 39B, 42C, 42D, 44D, 48B, 179B or 180B.
Foliation: Last 10 days of April at the above-growing location.
Flowering: Last 10 days of May to the middle of June in the above location.
Defoliation: With the cold temperatures in autumn after the fall of frost.
Hardiness: Hardy.
Tolerates: High summer temperatures as standard *Cornus kousa*; tolerates colder temperatures than standard *Cornus florida.*
Resistance: Medium resistance to diseases and insects.
General: This plant may be most easily propagated by grafting in the first ten days of April, or may be propagated by taking softwood cuttings for rooting from the middle to late June.

The most distinguishing characteristics of "Tsukuba-No-Mine" might be seen in its unusual presentation of delicate flowers over an extended blooming season, smaller leaves of unusual shape and margin characteristics, and its ability to develop into a delicately but densely branched specimen of moderate size and narrow upright figure, offering a distinctive specimen of excellent appearance for landscape use.

What is claimed is:

1. A new and distinct variety of white dogwood plant substantially as herein shown and described, characterized particularly as to novelty by the unique combination of (1) upright growth habit with thin branches and high branching characteristics; (2) small leaves; (3) flowering in a period from early to late June, over approximately 20 days; (4) blossoms being yellowish white; and (5) blossoms having thin patulous of narrow substantially lanceolate-shape of approximately 0.9 to 1.2 cm in width, and small diameter of approximately 6 to 7 cm.

* * * * *